Figure 1:
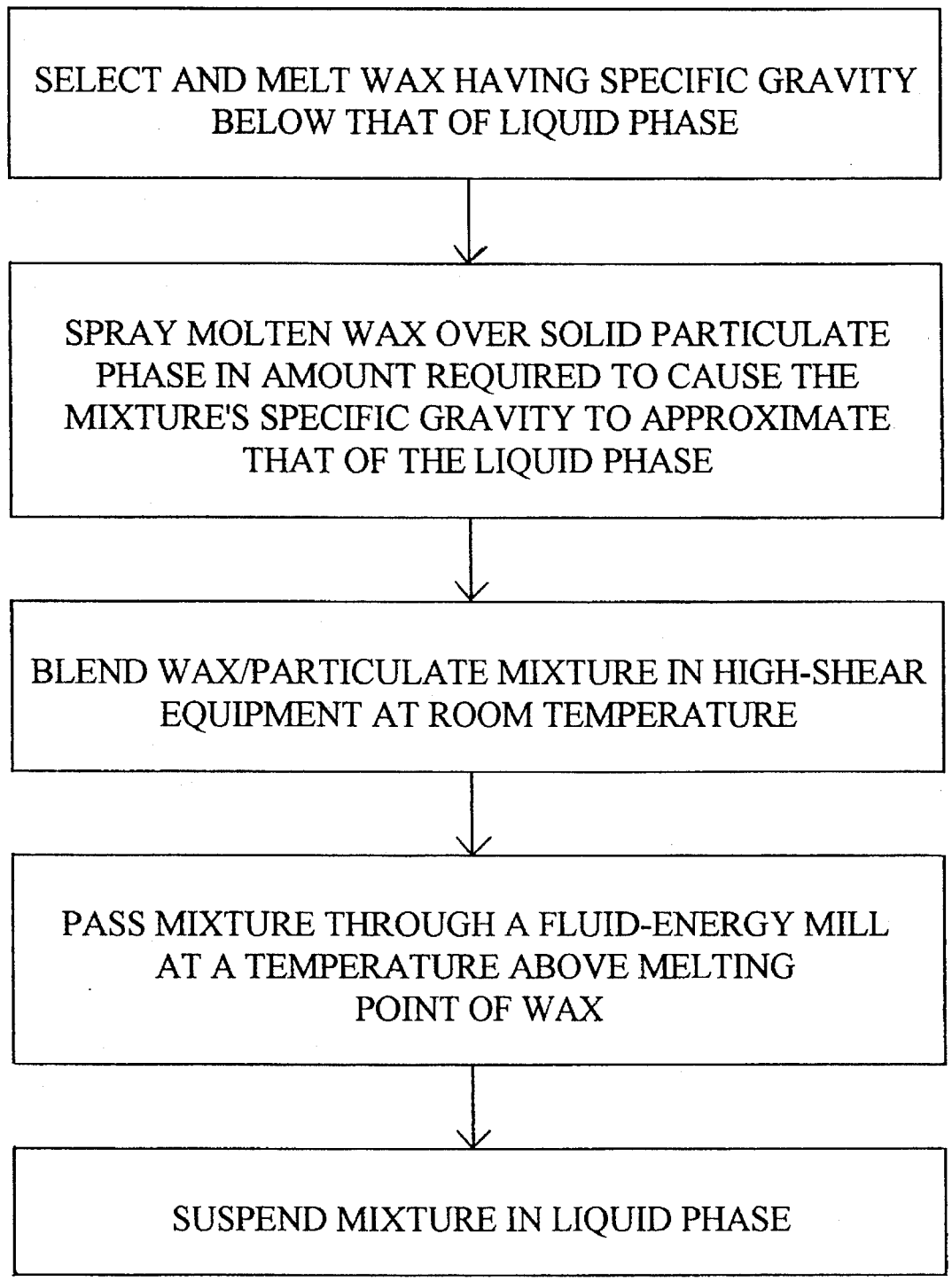
Figure 2:
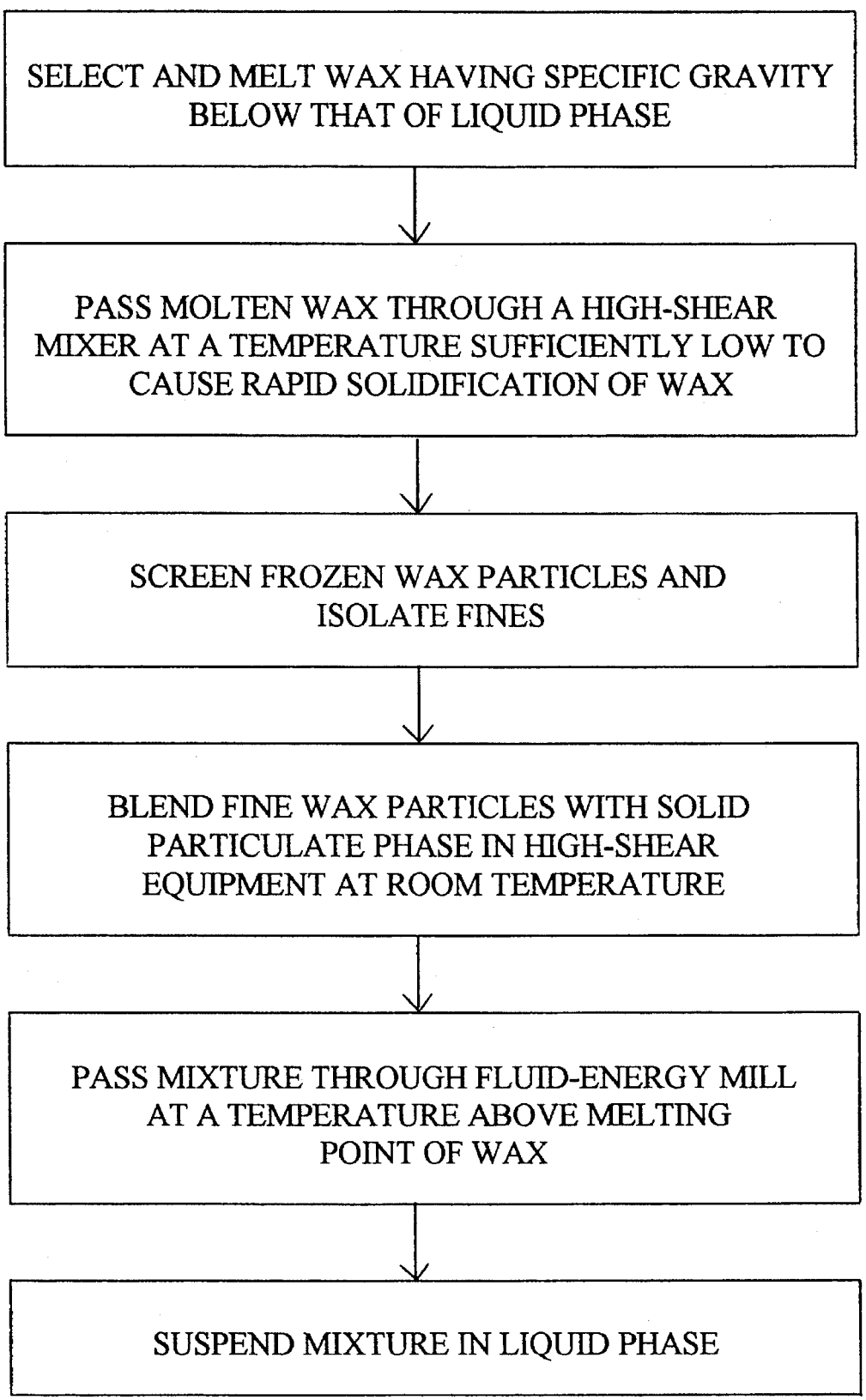

United States Patent [19]
Creech et al.

[11] Patent Number: 5,573,769
[45] Date of Patent: Nov. 12, 1996

[54] METHOD FOR SUSPENDING PARTICULATES IN LIQUIDS AND PRODUCTS RESULTING THEREFROM

[75] Inventors: David C. Creech; Jon S. Bach, both of Yuma, Ariz.

[73] Assignee: Gowan Company, Yuma, Ariz.

[21] Appl. No.: 185,210

[22] Filed: Mar. 18, 1994

[51] Int. Cl.$^6$ .......................... A01N 25/04; A01N 63/00; A01N 59/06; B01J 13/00

[52] U.S. Cl. .......................... 424/403; 424/705; 424/706; 424/632; 424/601; 424/676; 424/93.461; 252/311; 252/314; 514/80; 514/91; 514/602; 514/620; 71/DIG. 1

[58] Field of Search .............................. 252/313.1, 315.2, 252/302, 306, 311, 314; 424/420, 676, 682, 633, 93.461, 705, 405, 706, 632, 601; 427/212, 220; 264/45.4, 45.6; 71/DIG. 1; 106/122; 514/499, 500, 492, 602, 620, 80, 90

[56] References Cited

U.S. PATENT DOCUMENTS

| | | | |
|---|---|---|---|
| 2,884,352 | 4/1959 | Brenner et al. | 252/311 |
| 3,679,797 | 7/1972 | De Lange et al. | 71/DIG. 1 |
| 3,971,733 | 7/1976 | Hawkins | 252/311 |
| 4,166,112 | 8/1979 | Goldberg | 424/93 |
| 4,187,290 | 2/1980 | Goldberg | 424/93 |
| 4,707,359 | 11/1987 | McMullen | 424/92 |
| 4,834,894 | 5/1989 | Scheld | 252/49.9 |
| 5,059,334 | 10/1991 | Scheld | 252/32.5 |
| 5,190,764 | 3/1993 | Chiba et al. | 424/420 |
| 5,200,188 | 4/1993 | Mattox | 424/420 |
| 5,283,060 | 2/1994 | Shieh | 424/420 |
| 5,372,989 | 12/1994 | Geigle et al. | 504/116 |

OTHER PUBLICATIONS

*Hawley's Condensed Chemical Dictionary,* Van Nostrand Reinhold Co., Inc., NY,NY (1987) pp. 682 and 1239 1987.

Primary Examiner—Richard D. Lovering
Assistant Examiner—Daniel S. Metzmaier
Attorney, Agent, or Firm—Antonio R. Durando

[57] ABSTRACT

A method for coating finely divided particles with one or more hydrophobic materials, such as waxes, in order to envelope each particle with a thin layer of material that entraps air adhering to the surface of the particle. Because of the entrapped air, the apparent density of the particles is decreased and their stability in aqueous suspensions is greatly improved. When applied to pesticides, this process produces mixtures that remain substantially in suspension for several hours after agitation, thus allowing more uniform and trouble-free application.

26 Claims, 2 Drawing Sheets

METHOD FOR SUSPENDING PARTICULATES IN LIQUIDS AND PRODUCTS RESULTING THEREFROM

BACKGROUND OF THE INVENTION

1. Field of the Invention

This invention is related in general to liquid suspensions of small solid particles and, in particular, to a method for decreasing the apparent density of particulates dispersed in liquids, so as to improve their ability to remain in suspension.

2. Description of the Prior Art

Many commercial products consist of solid particles suspended in a liquid carrier for preservation and for ease of application. These products are not true colloids, inasmuch as the solid particles tend to separate out of the suspension within a relatively short period of time after mixing, thus creating problems of uniformity during application of the product. Therefore, it is necessary to stir the mixture vigorously to create a homogeneous suspension prior to, and sometimes even during, use. Examples of such products are some paints and pesticides that consist of solid active ingredients mixed in a liquid carrier. Therefore, this disclosure is presented with particular reference to pesticidal material for convenience, but it is not to be interpreted to be so limited in scope.

During commercial application, pesticides are usually pumped from a retaining tank in a moving vehicle through a system of articulated delivery pipes and spray nozzles. Typical pesticide formulations consist of suspensions that separate into two distinct phases rather rapidly, thus allowing the heavier particulate phase to settle at the bottom of the retaining tank and produce a non-homogeneous mixture. Thus, these products need to be mixed thoroughly before and during use to ensure uniform application and avoid clogging of the delivery system.

In order to increase the stability of solids suspended in liquids (sol-type colloidal suspensions), chemicals such as electrolytes may be added in the dispersing medium to provide attractive forces between the two phases and render the suspension intrinsically stable (that is, to create a lyophilic colloidal system). Another option is to reduce the size of the particulates because it is known that smaller particles form a more homogeneous mixture. As the size of the particles is reduced, the effects of surface phenomena become more important than the difference in density between the liquid and solid phases and gravity alone is not sufficient to cause separation. Stable colloidal behavior is usually associated with particles sizes ranging from $10^{-5}$ to $10^{-7}$ cm.

Pesticides typically contain larger active particles, in the $10^{-2}$–$10^{-5}$ cm range, which tend to settle out of dispersion in a few minutes. The particle size of the solid phase in these products cannot normally be altered without affecting the product itself and the addition of chemicals increases the cost of the product. Therefore, neither option is desirable. Accordingly, there still exists a need for a method of improving the stability of solid suspensions without affecting the chemical balance or the physical characteristics of the dispersed phase.

BRIEF SUMMARY OF THE INVENTION

One objective of this invention is a method for improving the stability of solid/liquid suspensions, thereby reducing the need for agitation of such mixtures prior to and during use.

Another goal of the invention is a method that does not affect the physical or chemical characteristics of the solid phase in suspension and that, therefore, does not alter the efficacy of the product.

Yet another goal is a method that can be applied in equivalent fashion to a variety of solid particles dispersed in a variety of media.

A final objective is a process that can be implemented easily and economically to produce suspensions according to the above stated criteria. This is achieved by using commercially available materials and manufacturing equipment, modified only to the extent necessary to fit the requirements of the invention.

Therefore, according to these and other objectives, the present invention consists of coating finely divided particles with one or more hydrophobic materials, such as wax, in order to envelope each particle with a thin layer of material that entraps air adhering to the surface of the particle. Because of the entrapped air, the apparent density of the particles is decreased and their suspension stability in aqueous media is greatly improved. When applied to pesticides, this process produces mixtures that remain substantially in suspension for several hours after agitation, thus allowing more uniform and trouble-free application.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

BRIEF DESCRIPTION OF THE DRAWINGS

FIG. 1 is a schematic representation of the steps involved in the process of the invention.

FIG. 2 is a schematic representation of the steps involved in an alternative process of the invention.

DETAILED DESCRIPTION OF THE INVENTION

Normally sol-type suspensions comprise a solid phase that is heavier than the liquid phase in which the solid particles are dispersed. As a result, the solid phase tends to separate out of the dispersion and settle at the bottom of the mixture. This phenomenon is particularly notable with water-based pesticides and paints. The present invention lies in the idea of matching the density of the solid phase to that of the liquid phase in such sol-type suspensions in order to stabilize the dispersion and increase the separation time between the two phases. In the case of heavier solids dispersed in aqueous media, this goal is achieved by coating the finely divided solid particles with a relatively light hydrophobic material, preferably a wax, so as to affect the particle's apparent density. Inasmuch as the surface of solid particulates is usually irregular, a thin coat of wax over the surface tends to envelop and entrap pockets of air (or any other gas, such as inert gases, present in the environment during the coating process), thus reducing the apparent density of the particles. By judiciously choosing the proper coating material and altering its characteristics to match the specific gravity of the particular liquid phase at hand, I found that the apparent density of the solid phase can be modified to approximately match that of the liquid phase, thus providing significant improvements in the stability of the suspension.

The process of coating the particles may be implemented in several ways that all yield acceptable results, so long as the surface of a substantial proportion of the particles is at least partially coated with a thin layer of material. For example, I used microcrystalline petroleum wax (such as is available from the Witco Corporation of New York, N.Y.) with a room-temperature specific gravity (20/20) of about 0.83 to 0.89 to coat synthetic powder cryolite (KSS standard grade from the Solvay Company of Germany) having a room-temperature specific gravity (20/20) of 2.95. Cryolite is an effective pesticide and is normally dispersed in a water medium having a specific gravity of about 1 for distribution and application to crops. Therefore, the objective was to reduce the apparent density of the cryolite powder to approach that of the water phase.

One approach consisted of raising the temperature of the wax above its melting point and spraying it onto the cryolite powder in an amount sufficient to reduce its apparent density to approximately the desired value (i.e., about 1). Since the effects of trapped air cannot be estimated with any certainty, the method required empirical testing to discover the best percentage of wax for the desired result, which of course generally depends on such factors as the particle size distribution of the solid medium and the density of the liquid phase. In the case of cryolite, mixtures of about 0.1 to 10.0 weight percent of wax (based on the total solid phase) were found to yield satisfactory results, the preferred range being 0.5 to 1.5 percent. After spraying, the cryolite/wax mixture was mechanically blended at room temperature to more uniformly spread the wax over the particle surfaces. A hammer mill was used for this step, but any high-shear equipment would be suitable to practice the invention. Finally, the mixture was passed through a turbulent stream of air or other gas at a temperature above the melting point of the wax (hot-air fluid energy milling), thus further spreading it as a thin film over the surface of each affected particle and trapping the air or gas present in the pockets resulting from coating over surface irregularities. The steps of this process are illustrated in the schematic chart of FIG. 1.

According to another approach, the microcrystalline wax was first melted and quickly re-solidified, such as by adding crushed ice or ice water, while being passed through a high-shear mixer (such as an Osterizer®). The frozen wax particles were then screened to separate the fraction smaller than 50 mesh and the product was air dried. Finally, the finer wax particles were blended with cryolite in a hammer mill and passed through a hot-air milling stage as described above. This approach produced coated cryolite that was indistinguishable from that of the first approach described above. The steps of this second approach are shown in the chart of FIG. 2.

As would be obvious to one skilled in the art, the operating temperature during the wax-melting step and hot-air milling step need not be much higher than the melting point of the wax used, so that its properties are not affected. For example, the microcrystalline petroleum wax used to coat cryolite has a melting point of 80° C. (176° F.) and was heated to about 93° C. (200° F.) during the described blending operation. Similarly, air and other gases, such as inert gases, may be mixed with the wax that is being sprayed onto the cryolite in order to form bubbles within the wax-film structure and produce a foam that further lightens the coating material. Thus, this treatment can be used as a further control over the apparent density of the solid phase resulting from the process of the invention.

Yet another equivalent approach consists of emulsifying melted wax in a water/amine/fatty-acid mixture. As is known in the art, such an emulsion may be prepared by first blending the wax with a fatty acid, such as stearic or oleic acid, where the acid is used in a concentration ranging from about 2 to 13 percent by weight. Then an amine, such as monoethanolamine, diethanolamine, triethanolamine, or morpholine, is added to water heated to a temperature above the melting point of the wax (for example, 205° F.). The amine should be used in an amine/fatty-acid mole ratio between 1:1 and 1:2. The amount of water used depends on the desired solid content; typically water is 20 to 40 percent by weight of the amine mixture. The wax/fatty-acid blend is then added to the amine/water mixture at approximately the same high temperature while continually agitating it to form a dispersion. Caution should be used to avoid whipping excess air into the emulsion because it is possible to make the particles lighter than water. For extended shelf life, the emulsion may be passed through a pre-heated homogenizer or equivalent device to obtain a particle size of about two microns. The emulsion is then allowed to cool to about 100 ° F. with continuous agitation. Finally, it is covered and allowed to cool to room temperature with continued agitation. If further dilution is needed, water is added to the emulsion while stirring. For good results, the total amount of emulsifying material should be approximately 5–25 percent of the total wax solids, 15 percent being preferred. The hot emulsion is then sprayed onto the cryolite particles (or other solid phase in aqueous dispersion) and subsequently hammer milled and hot-air milled as described above.

These methods of application are all suitable with waxes that smear relatively easily under shear force. For example, I found that microcrystalline petroleum wax and beeswax give good results with very rapid blending through a hammer mill and a hot-air mill, while other waxes, such as carnauba wax, require that greater shear force be applied during these steps, such as by multiple hammer milling. Wax blends obviously require intermediate degrees of milling. Other waxes and wax-like materials that can be similarly used for the invention consist of petroleum jelly, plant waxes, wool grease, cabbage wax, synthetic waxes, and gelled mineral oils (which produce a grease-like substance). Any of these, as well as petroleum wax, beeswax and carnauba wax, or mixtures thereof, can be applied onto the solid particles according to either of the methods described above, or methods equivalent to them.

The following examples illustrate the methods of the invention and the results derived therefrom.

EXAMPLE 1

Microcrystalline petroleum wax (from Witco) was heated to about 93° C. (200° F.) and sprayed onto cryolite powder having a particle size from to $10^{-4}$ cm to $10^{-2}$ cm (from Solvay) to produce an admixture containing 0.5 percent by weight of wax. The cryolite/wax mixture was then blended in a hammer mill to more uniformly spread the wax over the particle surfaces. Finally, the mixture was passed through a hot-air mill at about 93° C. (200° F.) to further spread the wax as a thin film over the surface of each cryolite particle. The coated cryolite was then mixed into water (in a concentration of about 15 percent by weight; the 10–25 percent range is typical for pesticides) for storage or for providing a dispersion vehicle during application.

EXAMPLE 2

The same microcrystalline petroleum wax was melted at about 93° C. (200° F.) and then passed through a high-shear mixer while adding crushed ice causing it to rapidly resolidify and break into small particles. The frozen wax particles were passed through a 50 mesh screen and the finer particles were air dried. The dry wax was then blended in a hammer mill to the same cryolite powder of Example 1 to produce a mixture containing 0.5 percent by weight of wax. Finally, the mixture was passed through a hot-air mill at about 93° C. (200° F.). The coated cryolite was then mixed into water for storage or application, as above.

EXAMPLES 2–6

The procedures of Examples 1 and 2 were repeated with the same microcrystalline wax and cryolite powder to produce mixtures containing 1.0 percent by weight and 2.0 percent by weight wax. The mixtures so produced and a batch of untreated standard cryolite were then stirred vigorously to form uniform suspensions and tested for stability. Each dispersion was allowed to rest in a graduated cylinder and settling times were measured as the solid phase separated from the liquid phase. Table 1 below compares the stability of the cryolite suspensions produced by the method of Example 1 with a standard cryolite product. The table shows the amount of mixed-phase height (a clear liquid phase being present above it) as a percentage of the total height of product in the graduated cylinder as a function of time after stirring.

TABLE 1

| Time Sec | Cryolite Standard | Cryolite 0.5% Wax | Cryolite 1.0% Wax | Cryolite 2.0% Wax |
|---|---|---|---|---|
| 0 | 100 | 100 | 100 | 100 |
| 15 | 90 | 100 | 100 | 100 |
| 30 | 82 | 99 | 99 | 100 |
| 60 | 77 | 97 | 98 | 99 |
| 75 | 71 | 95 | 98 | 98 |
| 90 | 64 | 95 | 97 | 97 |
| 105 | 59 | 93 | 97 | 96 |
| 120 | 51 | 93 | 95 | 95 |
| 135 | 48 | 90 | 94 | 94 |
| 150 | 45 | 90 | 93 | 93 |
| 165 | 41 | 90 | 92 | 92 |
| 180 | 39 | 89 | 91 | 91 |
| 195 | 38 | 89 | 90 | 90 |
| 240 | 30 | 87 | 90 | 89 |
| 300 | 27 | 82 | 89 | 87 |
| 420 | 22 | 78 | 80 | 80 |
| 600 | 20 | 70 | 60 | 70 |
| 18 min | | | 50 | |
| 22 min | | 50 | | |
| 25 min | | | | 50 |
| 1 hr 5 min | | | | 37 |
| 1 hr | | | 37 | |
| 1 hr 20 min | | 37 | | |

It is clear from Table 1 that the sedimentation times of treated cryolite were materially greater than for standard cryolite, thus yielding a more stable product for pumping and spraying during application to crops. For example, while standard cryolite settled to a height of approximately 70 percent after about 75 seconds, the coated products took between about 8 and 10 minutes to reach the same level of sedimentation. The results also show that the product coated with 0.5 percent of wax yielded the best sedimentation characteristics, although material differences between the three levels of coating began to occur only after the first 20 percent separation (at about 7 minutes from stirring).

The coated particles resulting from the coating method of Example 2 produced comparable results. In fact, the exact procedure by which wax or other wax-like material is smeared in thin films over the surface of small particles should not limit the scope of this invention. I found that any technique that results in a thin film of wax or equivalent material, whether foamed or not, being deposited to form a coat over the surface of small particles is suitable to practice the invention. Whether single or multiple hammer milling is used depends on the material being smeared and the facility with which it coats the solid particles. Similarly, whether fluid energy milling is used in combination with mechanical milling, or either is used alone, also depends on the specific requirements of the material utilized in the process.

Obviously, the coating process of the invention is only useful with pesticides if it does not adversely affect the pesticidal activity of the solid particulates. Thus, several tests were run to compare the effects of coated and uncoated products on several crops treated with normal pesticide applications. One test compared the efficacy of pesticides coated with various concentrations of microcrystalline wax with that of untreated cryolite on larvae growing on western grape leaves. The number of larvae per cane was counted on comparable canes at specific intervals of time and the condition of the larvae was recorded according to conventional observation methods. Thus, the pesticidal effect of cryolite (from Solvay) coated with 0.5%, 1.0% and 2.0% wax was compared to that of uncoated cryolite and to a check sample of untreated leaves. In addition, uncoated Kryocide® (a cryolite product from a different manufacturer, Atochem Corporation) and Dipel® (a *bacillus thuringensis* product sold by the Abbott Corporation) were also tested. The results are shown in Table 2 below.

TABLE 2

| Pesticide | Concentr. lb/Acre | Avg. Count of Larvae per Cane[1] (Days after Application) 0 | 2 | 4 | 7 | 11 |
|---|---|---|---|---|---|---|
| cryolite | 2 | 32.5 | 30.0 | 28.8 | 21.5 | 10.5 |
| standard | | | (1.5) | (1.5) | (2) | (2)[2] |
| cryolite | 4 | 26.7 | 31.7 | 28.3 | 19.7 | 13.0 |
| standard | | | (1.5) | (2) | (2) | (2) |
| cryolite | 2 | 23.3 | 20.0 | 15.5 | 6.7 | 2.3 |
| 0.5% Wax | | | (2) | (2) | (2) | (3) |
| cryolite | 4 | 20.0 | 11.8 | 4.0 | 1.8 | 1.5 |
| 0.5% Wax | | | (3) | (2) | (2) | (2) |
| cryolite | 2 | 35.0 | 35.0 | 20.0 | 16.5 | 11.5 |
| 1.0% Wax | | | (1.5) | (1.5) | (1.5) | (1.5) |
| cryolite | 4 | 30.0 | 25.0 | 17.5 | 15.5 | 13.0 |
| 1.0% Wax | | | (3) | (2) | (2) | (2) |
| cryolite | 2 | 14.0 | 12.7 | 13.0 | 6.7 | 2.0 |
| 2.0% Wax | | | (2) | (2) | (2) | (2) |
| cryolite | 4 | 11.7 | 6.8 | 5.0 | 2.3 | 1.3 |
| 2.0% Wax | | | (2) | (2) | (3) | (3) |
| Kryocide ® | 8 | 30.8 | 23.5 | 16.5 | 7.5 | 1.8 |
| (cryolite from Atochem Corp.) | | | (2) | (1.5) | (2) | (2) |
| Dipel ® | 1 | 52.5 | 45.0 | 12.0 | 7.5 | 1.8 |
| (bacillus thuringensis from Abbott Corp.) | | | (3) | (2) | (2) | (2) |
| Check | | 30.0 | 30.0 | 32.5 | 24.5 | 11.0 |

[1]Pretreatment random sampling of larval stages (5 total) on cane colonies:
Stage 2 = 3.4%
Stages 2–3 = 6.8%
Stages 2–4 = 27.6%
Stage 3 = 7.0%
Stages 3–4 = 37.9%
Stages 3–5 = 10.3%
Stage 4 = 3.5%
Stages 4–5 = 3.5%.
[2]Numbers circled indicate condition of larva after treatment:
1 = actively feeding
2 = scattered feeding and somewhat moribund
3 = obviously affected and moribund.

It is clear from these tests that the wax coating over all coated pesticides did not adversely affect their pesticidal activity. All coated pesticides showed comparable activity to the uncoated one and all pesticides produced a substantially greater decrease in larvae than the untreated check sample. Thus, this test demonstrated that the method of the invention may be used to coat pesticides without adversely affecting their performance.

The technique is equally applicable to coat any pesticide that is normally dispersed in a water medium, such as copper oxychloride, sulfur, phosmet, bensulide, Kryocide®, and dichloran. Similarly, the methods of the invention can be applied to coat paint pigments, which are usually much heavier than water. This practice would greatly reduce the frequency with which paints must be stirred during use, which has been a continuing problem in the paint industry. Thus, the cost of utilizing the methods of the invention to coat pigment particles would be justified by the added value to the resulting product. Obviously, other active ingredients may be added to the coating agent to achieve particular results, such as wetting agents, dispersing agents, odor-masking agents, or other materials that modify the properties of the product of interest.

Various changes in the details, steps and materials that have been described may be made by those skilled in the art within the principles and scope of the invention herein illustrated and defined in the appended claims. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and products.

We claim:

1. A method for improving the stability of a sol suspension consisting of a particulate solid phase dispersed in a liquid phase, wherein the solid phase has a specific gravity greater than a specific gravity of the liquid phase, comprising the following steps:
   (a) selecting a wax or petroleum jelly coating medium having a specific gravity less than the specific gravity of the liquid phase;
   (b) coating the particulate solid phase in a dried state with said coating medium so as to entrap gaseous matter adhering to said particulate solid phase and cause the particulate solid phase so produced having entrapped gas to acquire an apparent specific gravity approximately equal to the specific gravity of the liquid phase; and
   (c) dispersing the coated particulate solid phase having entrapped gas in the liquid phase to produce a stabilized suspension.

2. The method recited in claim 1, wherein said coating medium selected during step (a) is a wax with a melting point; and wherein said step (b) comprises
   melting the wax;
   spraying the molten wax over the particulate solid phase, thereby producing a wax/particulate mixture; and
   blending the wax/particulate mixture in a high-shear mixer.

3. The method recited in claim 2, wherein said step (b) further comprises the step of passing the blended wax/particulate mixture through a fluid-energy mill at a temperature above the melting point of the wax.

4. The method recited in claim 2, wherein said step (b) further comprises the step of mixing a gas to the molten wax during the process of spraying it over the particulate solid phase, so as to produce a foam in the wax.

5. The method recited in claim 2, wherein said particulate solid phase consists of pesticide particles having a diameter between $10^{-2}$ cm and $10^{-5}$ cm; and said liquid phase consists of an aqueous medium.

6. The method recited in claim 5, wherein said particulate solid phase is selected from the group consisting of cryolite, copper oxychloride, sulphur, phosmet, bensulide, dichloran, bacillus thuringensis, and mixtures thereof.

7. The method recited in claim 5, wherein said particulate solid phase consists of cryolite.

8. The method recited in claim 5, wherein said wax is selected from the group consisting of microcrystalline petroleum wax, beeswax, plant waxes, wool grease, synthetic waxes, or mixtures thereof; and
   is used in a concentration between 0.1 and 10.0 percent by weight of the total solid phase in the wax/particulate mixture; and
   wherein the steps of melting and spraying the wax are carried out at approximately 93° C.

9. The method recited in claim 1, wherein said coating medium selected during step (a) is a wax with a melting point; and wherein said step (b) comprises
   melting the wax;
   passing the molten wax through a first mixer at a temperature sufficiently low to cause the rapid solidification of the wax; and
   blending the solidified wax particles with the solid particulate phase in a second mixer, thereby producing a wax/particulate mixture.

10. The method recited in claim 9, wherein said step (b) further comprises the step of passing the blended wax/particulate mixture through a fluid-energy mill at a temperature above the melting point of the wax.

11. The method recited in claim 9, wherein said particulate solid phase consists of pesticide particles having a diameter between $10^{-2}$ cm and $10^{-5}$ cm; and said liquid phase consists of an aqueous medium.

12. The method recited in claim 11, wherein said particulate solid phase is selected from the group consisting of cryolite, copper oxychloride, sulphur, phosmet, bensulide, dichloran bacillus thuringensis, and mixtures thereof.

13. The method recited in claim 11, wherein said particulate solid phase consists of cryolite.

14. The method recited in claim 11, wherein said wax is selected from the group consisting of microcrystalline petroleum wax, beeswax, plant waxes, wool grease, synthetic waxes, and mixtures thereof; and is used in a concentration between 0.1 and 10.0 percent by weight of the total solid phase in the wax/particulate mixture; and wherein the steps of melting and spraying the wax are carried out at approximately 93° C.

15. The method recited in claim 1, wherein said coating medium selected during step (a) is petroleum jelly with a melting point; and wherein said step (b) comprises
   melting the petroleum jelly;
   spraying the molten petroleum jelly over the particulate solid phase, thereby producing a petroleum-jelly particulate mixture; and
   blending the petroleum-jelly/particulate mixture in a high-shear mixer.

16. The method recited in claim 15, wherein said particulate solid phase consists of pesticide particles having a diameter between $10^{-2}$ cm and $10^{-5}$ cm; and said liquid phase consists of an aqueous medium.

17. The method recited in claim 15, wherein said petroleum jelly is used in a concentration between 0.1 and 10.0 percent by weight of the total solid phase in the petroleum-jelly/particulate mixture; and wherein the steps of melting and spraying the petroleum jelly are carried out at approximately 93° C.

18. A sol suspension of a particulate solid phase having entrapped gas produced according to the method recited in claim 1.

19. A sol suspension of a particulate solid phase having entrapped gas produced according to the method recited in claim 2.

20. A sol suspension of a particulate solid phase having entrapped gas produced according to the method recited in claim 9.

21. A sol suspension of a particulate solid phase having entrapped gas produced according to the method recited in claim 3.

22. A sol suspension of a particulate solid phase having entrapped gas produced according to the method recited claim 4.

23. A sol suspension of a particulate solid phase having entrapped gas produced according to the method recited claim 10.

24. A sol suspension of a particulate solid phase having entrapped gas produced according to the method recited claim 11.

25. A sol suspension of a particulate solid phase having entrapped gas produced according to the method recited claim 15.

26. A sol suspension of a particulate solid phase having entrapped gas produced according to the method recited claim 17.

* * * * *